US010449383B2

(12) United States Patent
Mayr

(10) Patent No.: US 10,449,383 B2
(45) Date of Patent: Oct. 22, 2019

(54) MAGNETIC STIMULATION DEVICE

(71) Applicant: PonteMed AG, Teufen (CH)

(72) Inventor: Winfried Mayr, Mödling (AT)

(73) Assignee: PonteMed AG, Teufen (CH)

( * ) Notice: Subject to any disclaimer, the term of this patent is extended or adjusted under 35 U.S.C. 154(b) by 0 days.

(21) Appl. No.: 15/765,430

(22) PCT Filed: Sep. 29, 2016

(86) PCT No.: PCT/EP2016/073281

§ 371 (c)(1),
(2) Date: Apr. 2, 2018

(87) PCT Pub. No.: WO2017/055465

PCT Pub. Date: Apr. 6, 2017

(65) Prior Publication Data

US 2018/0280712 A1 Oct. 4, 2018

(30) Foreign Application Priority Data

Oct. 2, 2015 (AT) .............................. A 50839/2015

(51) Int. Cl.
*A61N 2/00* (2006.01)
*A61N 2/02* (2006.01)
(Continued)

(52) U.S. Cl.
CPC ............ *A61N 2/006* (2013.01); *A61B 5/0531* (2013.01); *A61H 39/007* (2013.01); *A61N 2/008* (2013.01);
(Continued)

(58) Field of Classification Search
CPC ........... A61N 2/006; A61N 2/008; A61N 2/02
See application file for complete search history.

(56) References Cited

U.S. PATENT DOCUMENTS 6,547,713 B1 * 4/2003 Talpo ........................ A61N 2/02 600/9
2006/0187607 A1 8/2006 Mo
(Continued)

FOREIGN PATENT DOCUMENTS

DE 3610474 A1 10/1986
DE 102012012149 A1 12/2013
(Continued)

OTHER PUBLICATIONS

Austrian Office Action Application No. A 50839/2015-1 completed: Apr. 1, 2016; dated Apr. 22, 2016 3 Pages.
(Continued)

*Primary Examiner* — Thaddeus B Cox
(74) *Attorney, Agent, or Firm* — Whitmyer IP Group LLC

(57) ABSTRACT

A device for magnetic stimulation of body regions, including at least one magnetic coil connected to a stimulator which has a power element for generating electrical impulses to be applied to the at least one magnetic coil, so that the generated magnetic field can be induced in the body region, wherein a detection unit is provided for detecting metal elements within the body region. A measuring device is provided for detecting the electrical power received by the magnetic coil and a comparison device is provided for comparing the power with a predetermined limit value, the detection unit is connected to the stimulator, and the comparison unit is designed to automatically switch off the stimulator or reduce the power of the stimulator or of the power element of the stimulator in the event of the predetermined limit value being exceeded.

17 Claims, 3 Drawing Sheets

(51) Int. Cl.
*A61B 5/053* (2006.01)
*A61H 39/00* (2006.01)
*A61N 7/00* (2006.01)

(52) U.S. Cl.
CPC ........ *A61N 2/02* (2013.01); *A61N 2007/0021* (2013.01)

(56) References Cited

U.S. PATENT DOCUMENTS

| | | | | | |
|---|---|---|---|---|---|
| 2008/0234534 | A1* | 9/2008 | Mikas | A61N 2/02 | 600/14 |
| 2008/0294036 | A1* | 11/2008 | Hoi | A61B 5/06 | 600/424 |
| 2010/0274223 | A1* | 10/2010 | Teitelbaum | A61B 17/064 | 604/507 |
| 2013/0150653 | A1* | 6/2013 | Borsody | A61N 2/006 | 600/13 |
| 2014/0257081 | A1* | 9/2014 | Rapoport | A61B 5/062 | 600/409 |
| 2015/0238118 | A1* | 8/2015 | Legassey | A61B 5/062 | 600/347 |

FOREIGN PATENT DOCUMENTS

| | | | |
|---|---|---|---|
| EP | 0617982 | A1 | 10/1994 |
| EP | 2462869 | A1 | 6/2012 |
| WO | 2008025937 | A2 | 3/2008 |
| WO | 2009126117 | A1 | 10/2009 |

OTHER PUBLICATIONS

PCT International Preliminary Report on Patentability Application No. PCT/EP2016/073281 dated Oct. 31, 2017 6 Pages.

PCT International Preliminary Examination Application No. PCT/EP2016/073281 dated Sep. 12, 2017 6 Pages.

PCT International Written Opinion of the International Searching Authority Application No. PCT/EP2016/073281 dated Oct. 2, 2015 5 Pages.

* cited by examiner

MAGNETIC STIMULATION DEVICE

TECHNICAL FIELD

The present teaching relates to a device for magnetic stimulation of regions of a human or animal body, comprising at least one magnetic coil connected to a stimulator which has a power element for generating electrical impulses to be applied to the at least one magnetic coil, so that the magnetic field generated in the at least one magnetic coil can be induced in the body region, wherein a detection unit is provided for detecting metal elements within the body region in which the magnetic field is induced, and the detection unit is connected to a display unit and the stimulator.

BACKGROUND

In contrast to functional electrical stimulation (FES) where a muscle or nerve, for performing muscle contraction or for influencing other nerve functions, is stimulated electrically via contacting electrodes so as to support and/or replace particular physiological processes, in the functional magnetic stimulation (FMS) a nerve activation which may, for instance, lead to a muscle contraction, is triggered without contact by appropriate magnetic fields.

The functional magnetic stimulation has the substantial advantage over the functional electrical stimulation with electrodes disposed on the skin surface that pain sensors being within the skin are activated substantially less and the use is felt to be much more comfortable while comparable neuromuscular activation takes place. This is due to the fact that the pain sensors are in high-impedance tissue layers as compared to lower tissue portions. The current flow with electrical stimulation thus causes relatively high electric field strengths especially in the field of pain sensors while the effect-relevant induced eddy currents in the case of magnetic stimulation are substantially stronger in the low-impedance lower tissue than in the high-impedance tissue closer to the surface.

Furthermore, in the case of the functional magnetic stimulation the effort and the risk is, due to the lapse of the implantation of nerve or muscle electrodes which is frequently necessary with the functional electrical stimulation, substantially lower and the acceptance is higher. Contrary to this, however, the targeted stimulation of particular nerves or muscles via the magnetic field is more difficult than with the direct electrical stimulation by means of skin electrodes or implanted electrodes. It is especially very difficult when stimulating lower regions to reach particular points, so-called motor points, with the magnetic field and to achieve, for instance, the contraction of the desired muscles.

Another disadvantage of the functional magnetic stimulation are metal elements within the body region to be stimulated, in which inadmissibly high currents are induced and a dangerous heating of the metal elements and of the surrounding tissue may occur. As examples of such metal elements implants, artificial joints, or the like are mentioned.

An example of a device for magnetic stimulation is described in WO 2009/126117 A1. Here, a magnetic field is induced in lower tissue layers by means of a magnetic coil, which results in a depolarization of neuronal cells leading to muscle contractions of particular muscles in particular body regions.

Another method and a device for neuromagnetic stimulation has become known from EP 0 617 982 A1, wherein a focused ultrasonic beam is superimposed to the magnetic field, with the intention of enabling a more precise spatial stimulation.

A method and a device for pelvic floor training by means of magnetic stimulation has, for instance, become known from DE 10 2012 012 149 A1. In addition to magnetic stimulation, the tissue is supplied with oxygen and/or ozone to further support the training and the build-up of muscles.

US 2013/150653 A1 describes a generic device for magnetic stimulation, wherein a detection unit for detecting metal elements within the treated body region in which the magnetic field is induced is disclosed in the form of own measuring coils.

SUMMARY

The object of the present teaching therefore consists in providing an above-mentioned magnetic stimulation device by which a dangerous heating of metal elements within the body region in which the magnetic field is induced can be prevented efficiently. Disadvantages of known stimulation devices are to be avoided or at least reduced.

One object according to the present teaching is solved in that a measuring device is provided for detecting the electrical power received by the at least one magnetic coil in response to a test signal fed in the magnetic coil by measuring the amount and the phase of the current and the voltage at the magnetic coil, and a comparison device is provided for comparing the received electrical power with a predetermined limit value set during a preceding calibration, and the comparison device is designed to automatically switch off the stimulator or reduce the power of the stimulator or of the power element of the stimulator in the event of the predetermined limit value being exceeded, and that at least one further detection unit is provided which is formed by at least one ultrasonic transmitter and at least one ultrasonic receiver, an evaluation unit, and/or by at least two skin electrodes and a device for measuring the tissue impedance of the respective body region. The detection of metal elements via the electrical power received by the at least one magnetic coil is an elegant integrated solution of a detection unit in which few additional components are required since the detection of the metal elements is detected by the feedback to the magnetic coil of the stimulation device. The detection of the electrical power received by the magnetic coil and the comparison with corresponding limit values may be implemented in a relatively simple and cost-efficient manner in the magnetic stimulation device with a microprocessor or the like which is usually available anyway. By the detection unit included in the magnetic stimulation device it is thus possible to at least indicate the presence of metal elements within the body region to be treated and a change of position of the stimulation device may, for instance, be made before the stimulation is started. Thus, it is possible to prevent an inadmissible and dangerous heating of the metal elements or implants by detecting the presence of metal elements. Thus, the quite substantial risk of potential tissue-damaging heating or damage to medical implants can be reduced largely. So far, this has only been avoidable by careful and comprehensive accompanying medical clarification and/or by performing radiography prior to stimulation.

By the fact that the detection unit is connected to the stimulator it is possible, when detecting metal elements within the body region in which the magnetic field is to be induced, to automatically deactivate the stimulator or its power element, or to reduce the power so as to safely prevent inadmissible heating of the metal elements or implants.

This variant is an elegant integrated solution of a detection unit in which few additional components are required since the detection of the metal elements is performed by the feedback to the magnetic coil of the stimulation device. The detection of the electrical power received by the magnetic coil and the comparison with corresponding limit values may be implemented in a relatively simple and cost-efficient manner in the magnetic stimulation device with a microprocessor or the like which is usually available anyway.

Additionally to the indirect detection of metal elements via the power received by the at least one magnetic coil at least one further detection unit is provided which may be formed by at least one ultrasonic transmitter and at least one ultrasonic receiver and an evaluation unit. Such implementation of the further detection unit is indeed characterized by a higher hardware-technical effort, but can detect corresponding metal elements in the body with higher preciseness.

Alternatively or additionally the further detection unit may also be formed by at least two skin electrodes and a device for measuring the tissue impedance of the respective body region. By applying a particular current or a particular voltage via the at least two skin electrodes, for instance, adhesive electrodes, and by calculating the resulting tissue impedance, the presence of implants or the like in the body can be detected even better in a relatively reliable manner and with little technical effort.

Finally, the further detection unit may also be formed by at least one measuring coil. By means of a measuring coil differing from the stimulation coil and having a number of windings differing from the stimulation coil and a differing frequency behavior it is also possible to detect, in the kind of a metal detector, implants or the like in the body region to be stimulated prior to performing the stimulation. In order to prevent an induction of the magnetic field of the at least one magnetic coil in the at least one magnetic coil and correspondingly high damaging currents, the measurement may also be made prior to performing the stimulation, and subsequently the measuring coil may be deactivated.

The display unit may be formed by an optical display unit. Such optical display unit may, in the simplest case, be implemented by at least one light emitting diode or the like, or may else be formed by a more complex display unit such as, for instance, an LCD panel. The optical display unit indicates the presence of metal elements within the patient's body region to be stimulated to the respective operating personnel, so that a change of position of the at least one magnetic coil can be made prior to performing the stimulation.

Likewise, the display unit may be formed by an acoustic display unit. On its own or in addition to the optical display unit such an acoustic display unit may signal the user the presence of metal elements in the body region to be stimulated by outputting acoustic signals.

Finally, the display unit may also be formed by a mechanical oscillator to indicate to the user or to the patient by appropriate vibrations that repositioning of the at least one magnetic coil is to be performed.

Advantageously the at least one magnetic coil is disposed in a housing. An appropriate housing insulates the magnetic coil safely from being touched and protects it from damage, on the one hand, and facilitates the applying of the magnetic coil at the respective body region and also facilitates cleaning and/or disinfecting of the components of the stimulation device, on the other hand.

Also the detection unit and possibly the at least one further detection unit may be disposed in the housing. This achieves a more compact construction and ensures that the metal elements are really detected in the region in which the magnetic field is effective for stimulation.

BRIEF DESCRIPTION OF THE DRAWINGS

The present teaching will be explained in detail by means of the enclosed drawings. There show.

DETAILED DESCRIPTION

Figure 1:
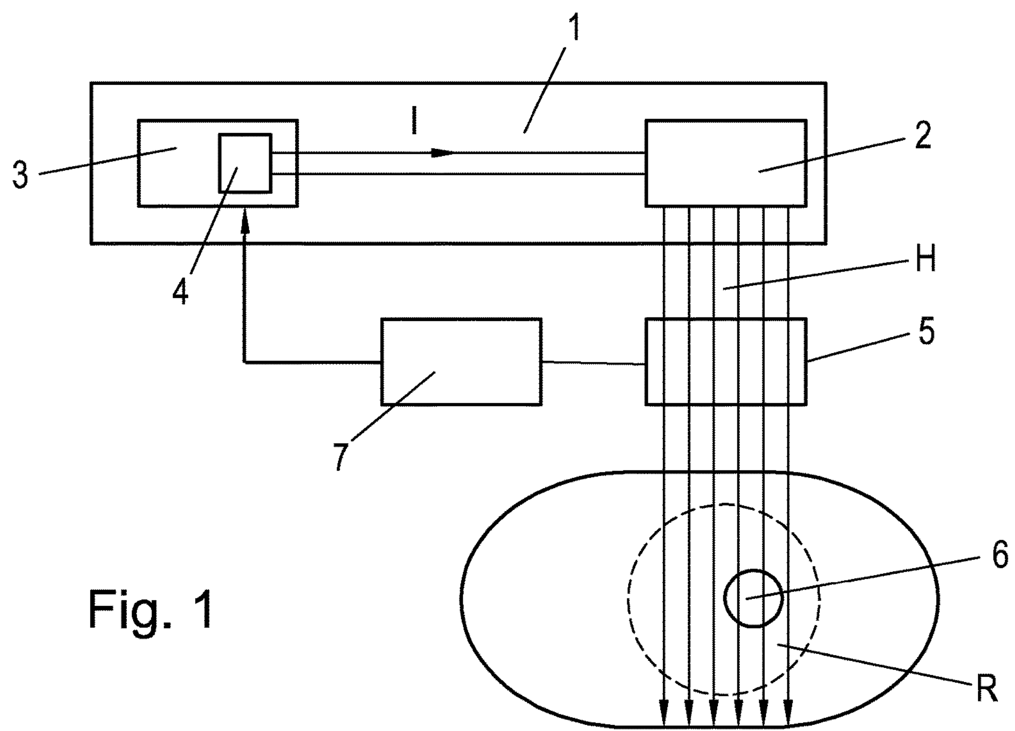
FIG. 1 a block diagram of a magnetic stimulation device with a detection unit in a general form.

FIG. 1 illustrates a block diagram of a magnetic stimulation device 1 comprising a detection unit 5 in a general form. The device 1 for magnetic stimulation of regions R of a human or animal body comprises at least one magnetic coil 2 connected to a stimulator 3 which has a power element 4 for generating electrical impulses I which are applied to the at least one magnetic coil 2. The electrical impulses I produce in the at least one magnetic coil 2 a magnetic field H which is induced in the body region R and causes effects at desired points, e.g. at so-called motor points, which may lead to muscle contractions of the desired body region R or influence other nerve functions. The term impulses includes both rectangular impulses and other current forms by which alternating fields are produced in the magnetic coil 2. If metal elements 6 such as e.g. implants, bone screws or the like, are disposed in the respective body region R in which the magnetic field H of the at least one magnetic coil 2 is induced, the magnetic field H of the at least one magnetic coil 2 can induce eddy currents in these metal elements 6 which may lead to a dangerous heating of the metal elements 6. Already if approx. 43° C. are exceeded, a denaturation of the protein shares in the surrounding tissue of the body region R and dramatic tissue damages may occur. It is therefore particularly important to clarify prior to the activation of the stimulation device 1 whether metal elements 6 are present in the body region R to be stimulated. In accordance with the present teaching this is performed by means of a detection unit 5 which detects the presence of metal elements 6 and displays or renders same optically or acoustically at a display unit 7 and causes direct influencing of the stimulator 3 or the power unit 4 and hence a regulation of the stimulation impulses I for the at least one magnetic coil 2, which is shown by the connection line between the display unit 7 and the stimulator 3. By means of the detection unit 5 it is possible to perform a magnetic stimulation with high security without having to accept the risk of tissue damages even without previous clarification with the patient and/or without performing radiography.

Figure 2:
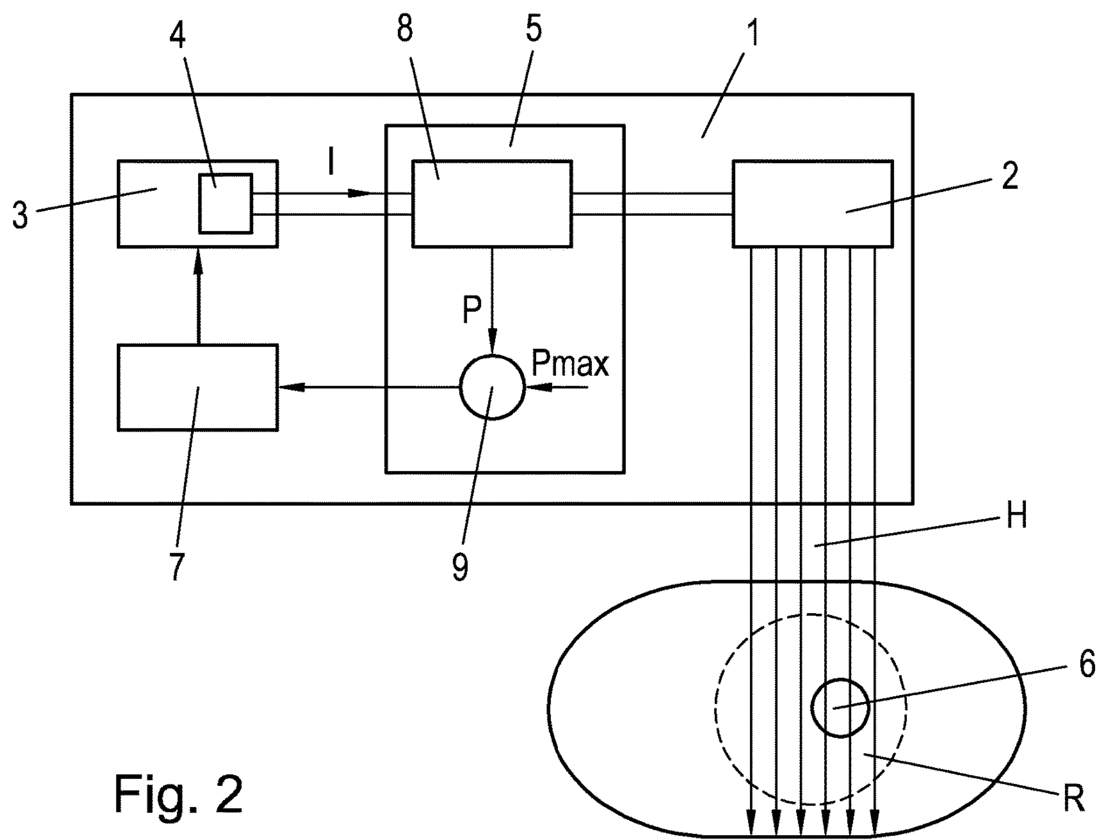
FIG. 2 a block diagram of the magnetic stimulation device with the variant of the detection unit in accordance with the present teaching, said detection unit deriving the existence of metal elements in the body region from the electrical power received by the magnetic coil.

FIG. 2 illustrates a block diagram of the magnetic stimulation device 1 with the variant of the detection unit 5 in accordance with the present teaching, which derives the presence of metal elements 6 present in the body region R from the electrical power received by the magnetic coil 2. In this process, the electrical power P received by the at least one magnetic coil 2 is detected by a measuring device 8 and supplied to a comparison device 9 which performs a comparison of the measured electrical power P with a predetermined limit value $P_{max}$. If the electrical power P received by the at least one magnetic coil 2 exceeds the predetermined limit value $P_{max}$, this results in an optical or acoustic representation at the display unit 7 or in an automatic switch-off or power reduction of the stimulator 3 or of the power element 4 of the stimulator 3.

The detection of metal elements 6 via the power received by the magnetic coil 2 may be performed by detecting the reaction of the magnetic coil 2 on the stimulation impulses or corresponding test signals. As stimulation impulses individual periods of sinusoidal signals are commonly used. As test signals especially sinusoidal signals of low amplitude with changing frequency are particularly suited. In response, the amount and phase of current and voltage are measured at the magnetic coil 2 and thus the complex impedance of the magnetic coil is determined. By the presence of metal elements within the magnetic field of the magnetic coil 2 this impedance changes, which is detected with the method in accordance with the present teaching. The measurement of the response of the magnetic coil 2 to the stimulation signal or a test signal may also be preceded by a calibration in which no object is present in the region of the magnetic coil 2. By this calibration it is possible to better adjust the limit value from which switch-off or power reduction of the stimulator 3 or of the power element 4 of the stimulator 3 is to take place. Instead of a test signal of changing frequency a rectangular impulse may also be used which has correspondingly many frequencies in the spectrum.

In this embodiment variant the detection unit 5 and the display unit 7 are integrated into the stimulation device 1.

Figure 3:
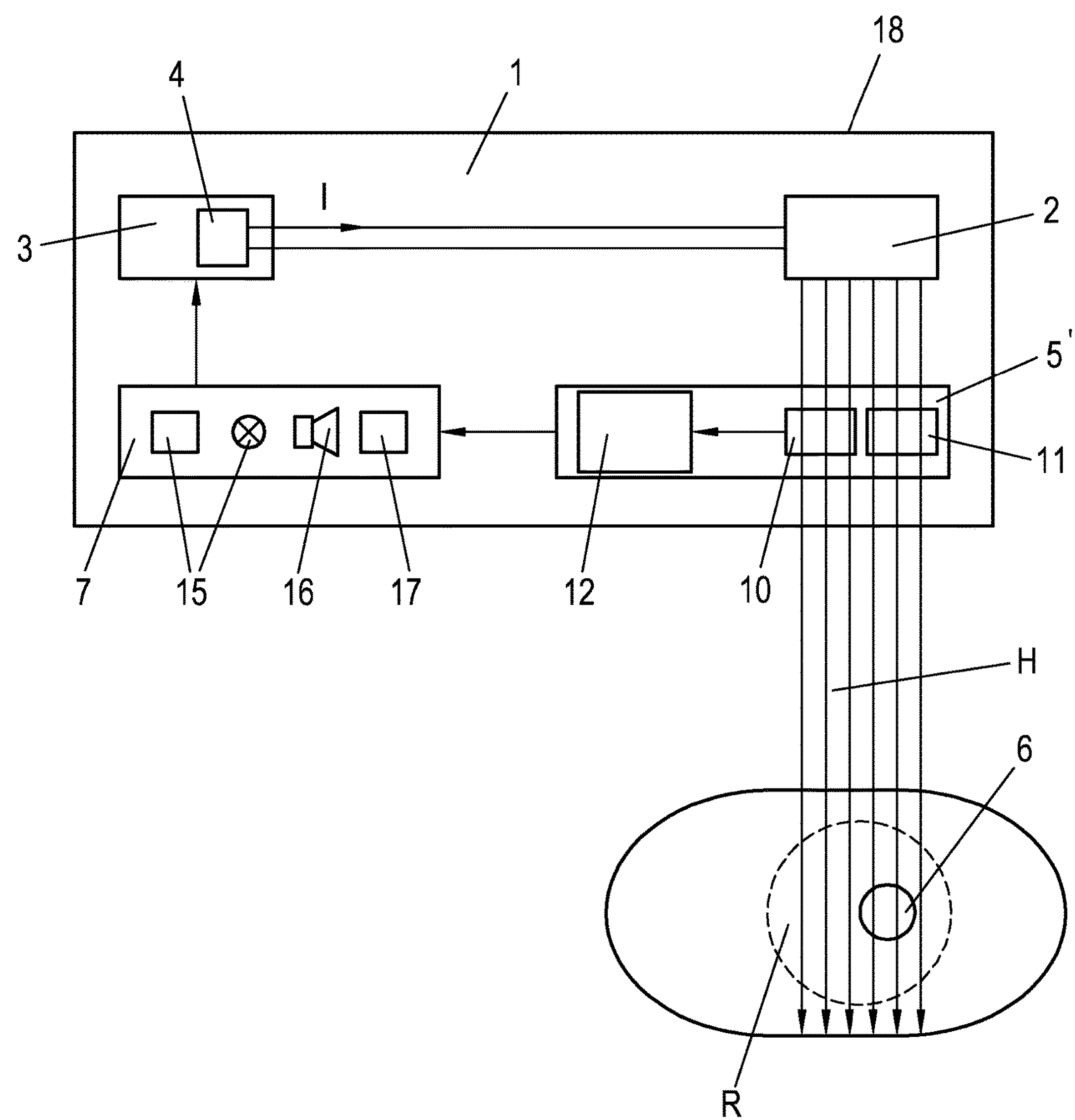
FIG. 3 a block diagram of the magnetic stimulation device with a variant of a further detection unit with ultrasonic transmitters and receivers.

FIG. 3 illustrates a block diagram of the magnetic stimulation device 1 with a variant of a further detection unit 5' comprising ultrasonic transmitters 10 and receivers 11. By a suitable arrangement of the ultrasonic transmitters 10 and the ultrasonic receivers 11 and an appropriate evaluation in an evaluation unit 12 it is possible to even better detect the presence of metal elements 6 within the body region R in which the magnetic field H of the at least one magnetic coil 2 is to be induced. The evaluation unit 12 is connected to the display unit 7 so as to be able to represent the result of the detection at the display unit 7.

The display unit 7 may be formed by an optical display unit 15, for instance, light emitting diodes or an LCD screen or the like. Furthermore, it may be implemented by an acoustic display unit 16 and/or by a mechanical oscillator 17 which may, for instance, also be accommodated in a handle for the positioning of the magnetic coil 2 (not illustrated).

The at least one magnetic coil 2 for performing functional magnetic stimulation may be disposed in a housing 18 in which the detection unit 5 and the further detection unit 5' and the display unit 7 are preferably also accommodated. By the arrangement in a common housing 18 the cleaning of the device 1 is facilitated and the allocation of the stimulation elements and the detection elements is ensured.

Figure 4:
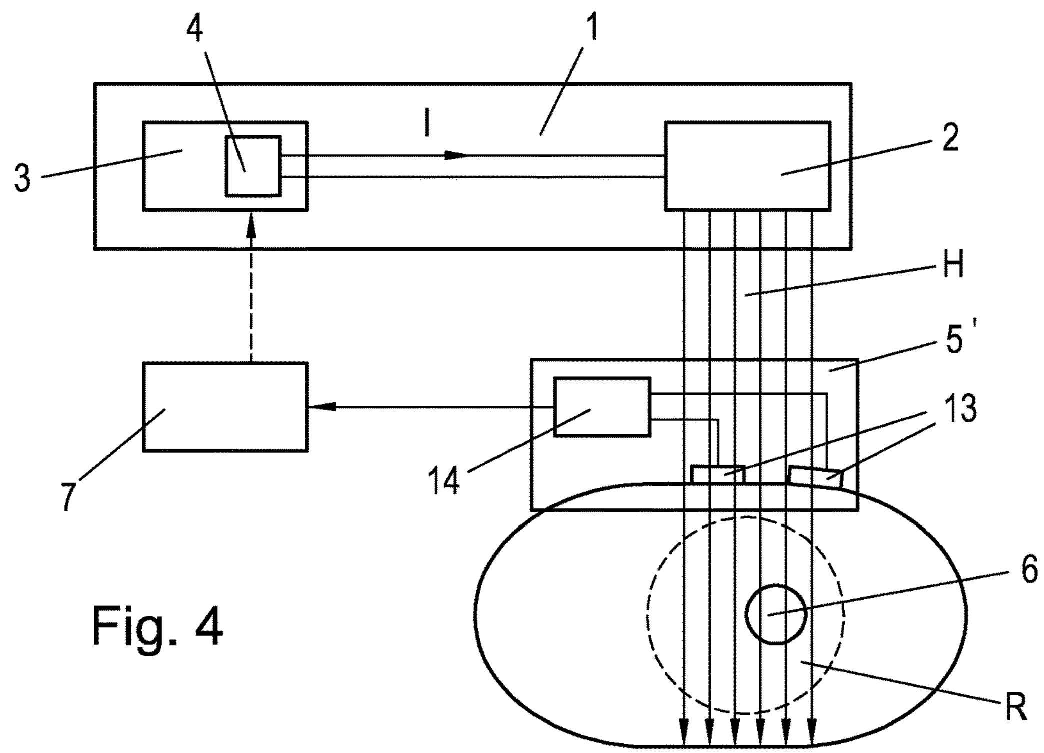
FIG. 4 a block diagram of the magnetic stimulation device with a variant of a further detection unit with skin electrodes and impedance measurement.

FIG. 4 illustrates a block diagram of the magnetic stimulation device 1 with a variant of a further detection unit 5' with skin electrodes 13 and measurement of the tissue impedance Z. This possible additional embodiment of the further detection unit 5' is characterized by the applying of current or voltage via the skin electrodes 13 and a measurement device 14 measuring the tissue impedance Z of the respective body region R. If the tissue impedance Z falls below particular threshold values, this may be an indication of the presence of metal elements 6 within the body region R, which results in a corresponding display at the display unit 7. As skin electrodes 13 adhesive electrodes or metal electrodes are possible. They may be integrated in a housing in which the at least one magnetic coil 2 for stimulation is disposed, or may also be disposed in their own housing separate from the stimulation device 1.

Figure 5:
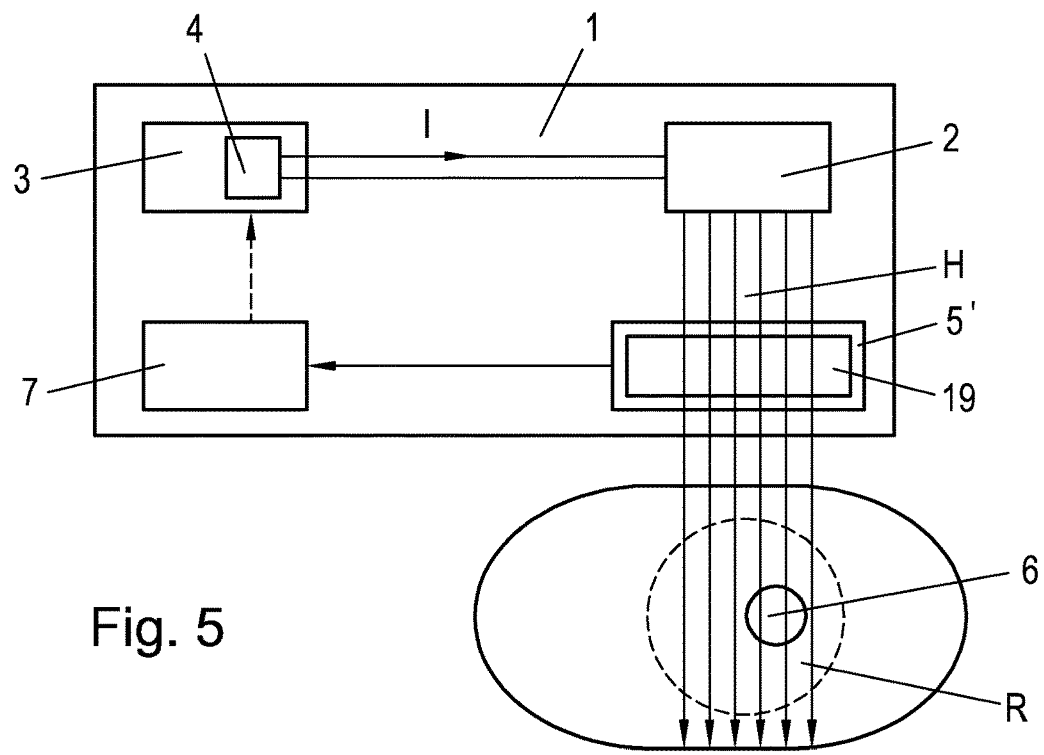
FIG. 5 a block diagram of the magnetic stimulation device with a variant of a further detection unit in the form of a measuring coil.

Finally, FIG. 5 illustrates a block diagram of the magnetic stimulation device 1 with a variant of a further detection unit 5' in the form of a measuring coil 19. In this embodiment variant the metal element 6 is detected in the body region R by means of at least one measuring coil 19 in the kind of a metal detector, and a corresponding warning is represented at the display unit 7 and possibly a control signal is sent to the stimulator 3. The measuring coil 19 differs with respect to construction and number of windings distinctly from the at least one magnetic coil 2 for producing the magnetic field H which is to be induced in the body region R. In this embodiment variant the components of the further detection unit 5' and of the display unit 7 are again disposed in the magnetic stimulation device 1.

The detection unit 5 in accordance with the present teaching may be integrated in a magnetic stimulation device 1 or be incorporated in existing magnetic stimulation devices 1 as an add-on kit. No interference in the power element 4 of the stimulator 3 of the stimulation device 1 is mandatorily necessary, but the response of the magnetic coil 2 to the stimulation impulse or a test impulse may also take place only by measuring the voltage and the current at the supply lines to the magnetic coil 2. For this purpose, only appropriate lines for tapping the voltage at the supply lines to the magnetic coil 2 and a current transformer for detecting the current are required.

An alternative method of detection of metal elements within the magnetic field of a magnetic coil via the power received by the magnetic coil may also be performed by indirect measurement of the residual voltage at a storage capacitor which is charged to a high voltage prior to each impulse output and stores the necessary energy, as it is commonly used for generating the stimulation impulses. Due to the influence of metal elements within the magnetic field of the magnetic coil the impedance of the magnetic coil and hence the residual voltage at the capacitor for generating the stimulation impulse after the output of the stimulation impulse changes. This latter-mentioned method, however, requires interference in the power element of the stimulator of the stimulation device.

The invention claimed is:

1. A device for magnetic stimulation of regions of a human or animal body, comprising at least one magnetic coil connected to a stimulator which has a power element for generating electrical impulses to be applied to the at least one magnetic coil, so that a magnetic field generated in the at least one magnetic coil can be induced in a body region, wherein a measuring device is provided for the detection of metal elements using electrical power received by the at least one magnetic coil, in response to a test signal fed in the magnetic coil to induce the magnetic field in the body region, by measuring an amount and a phase of a current and a voltage at the magnetic coil, and a comparison device is provided for comparing the received electrical power with a predetermined limit value set during a preceding calibration, and the comparison device is designed to automatically switch off the stimulator or reduce a power of the stimulator or of the power element of the stimulator in the event of the predetermined limit being exceeded.

2. The magnetic stimulation device according to claim 1, further comprising at least one measuring coil.

3. The magnetic stimulation device according to claim 1, further comprising an optical display unit.

4. The magnetic stimulation device according to claim 1, wherein the at least one magnetic coil is disposed in a housing.

5. The magnetic stimulation device according to claim 4, wherein the measuring device and comparison device are disposed in the housing.

6. The magnetic stimulation device according to claim 1, further comprising a mechanical oscillator.

7. A method of providing magnetic stimulation to a body region of a human or animal body using a stimulation device, comprising:

providing the device of claim 1;

feeding the test signal in the magnetic coil;

measuring the electrical power received by the magnetic coil in response to the test signal;

comparing the electrical power received by the magnetic coil with the predetermined limit value;

in the event the predetermined limit is exceeded, automatically reducing the power of the stimulator.

8. The magnetic stimulation device according to claim 1, comprising at least one ultrasonic transmitter and at least one ultrasonic receiver for the detection of metal elements within the body region.

9. The magnetic stimulation device according to claim 1, comprising at least two skin electrodes for the detection of metal elements within the body region.

10. A device for magnetic stimulation of a body region of a human or animal body, comprising:

a magnetic coil connected to a stimulator having a power element for generating electrical impulses to be applied to the magnetic coil, such that a magnetic field generated in the magnetic coil is induced in a body region;

a measuring device detecting metal elements using electric power received by the magnetic coil, in response to a test signal fed in the magnetic coil to induce the magnetic field in the body region, by measuring an amount and a phase of a current and a voltage at the magnetic coil;

a comparison device comparing the electrical power received by the magnetic coil with a predetermined limit value set during a preceding calibration, and, in the event the predetermined limit is exceeded, automatically switching off the stimulator or reducing a power of the stimulator.

11. The magnetic stimulation device according to claim 10, wherein:

the stimulator, magnetic coil, measuring device, and comparison device are all disposed in a housing.

12. The magnetic stimulation device according to claim 10, further comprising an ultrasonic transmitter and an ultrasonic receiver.

13. The magnetic stimulation device according to claim 10, further comprising at least two skin electrodes.

14. The magnetic stimulation device according to claim 10, further comprising a display unit indicating the detection of metal elements.

15. A method of providing magnetic stimulation to a body region of a human or animal body using a stimulation device, comprising:

a magnetic coil connected to a stimulator having a power element for generating electrical impulses to be applied to the magnetic coil, such that a magnetic field generated in the magnetic coil is induced in a body region;

a measuring device for detecting metal elements using electrical power received by the magnetic coil, in response to a test signal fed in the magnetic coil to induce the magnetic field in the body region, by measuring an amount and a phase of a current and a voltage at the magnetic coil;

a comparison device for comparing the electrical power received by the magnetic coil with a predetermined limit value set during a preceding calibration, and, in the event the predetermined limit is exceeded, automatically switching off the stimulator or reducing a power of the stimulator;

the method comprising:

feeding the test signal in the magnetic coil;

measuring, with the measuring device, the electrical power received by the magnetic coil in response to the test signal;

comparing, with the comparison device, the electrical power received by the magnetic coil with the predetermined limit value set during a preceding calibration;

in the event the predetermined limit is exceeded, automatically switching off the stimulator or reducing the power of the stimulator.

16. The method according to claim 15, wherein:

the stimulator and magnetic coil are all disposed in a housing.

17. The method according to claim 15, wherein:

in the preceding calibration no object is detected in a region of the magnetic coil.

* * * * *